US009949229B2

(12) United States Patent
Kubota et al.

(10) Patent No.: US 9,949,229 B2
(45) Date of Patent: Apr. 17, 2018

(54) ELECTRONIC DEVICE

(71) Applicant: NIKON CORPORATION, Tokyo (JP)

(72) Inventors: Yukio Kubota, Tsurugashima (JP); Satoshi Ejima, Tokyo (JP); Takeo Motohashi, Matsudo (JP); Mitsuko Matsumura, Sagamihara (JP); Hiroki Ono, Kawasaki (JP); Masakazu Sekiguchi, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/078,500

(22) Filed: Mar. 23, 2016

(65) Prior Publication Data
US 2016/0205658 A1 Jul. 14, 2016

Related U.S. Application Data

(63) Continuation of application No. 14/361,614, filed as application No. PCT/JP2012/079254 on Nov. 12, 2012, now Pat. No. 9,337,900.

(30) Foreign Application Priority Data

Dec. 12, 2011 (JP) ................. 2011-271542
Dec. 12, 2011 (JP) ................. 2011-271543
Dec. 12, 2011 (JP) ................. 2011-271544

(51) Int. Cl.
*H04W 64/00* (2009.01)
*H04B 5/00* (2006.01)
(Continued)

(52) U.S. Cl.
CPC ......... *H04W 64/006* (2013.01); *A61B 5/0028* (2013.01); *A61B 5/1122* (2013.01);
(Continued)

(58) Field of Classification Search
CPC .......................... H04B 5/0031; H04W 64/006
See application file for complete search history.

(56) References Cited

U.S. PATENT DOCUMENTS 6,924,846 B2 * 8/2005 Ohba ................. H04N 5/44504
345/633
2008/0200310 A1 8/2008 Tagliabue
(Continued)

FOREIGN PATENT DOCUMENTS

CN 101246518 A 8/2008
JP H06-83063 U 11/1994
(Continued)

OTHER PUBLICATIONS

Apr. 11, 2016 Office Action issued in Russian Application No. 2014123710.
(Continued)

*Primary Examiner* — Tuan H Nguyen

(57) ABSTRACT

To improve the usability of an electronic device, the electronic device includes: a first communication unit located near a user; a receive unit configured to receive data through communication via a body of the user or near field communication between a second communication unit located in a member used by the user and the first communication unit; and a recording unit configured to record data pertaining to the member when communication is established between the first communication unit and the second communication unit.

21 Claims, 10 Drawing Sheets

(51) Int. Cl.

| | | |
|---|---|---|
| H04W 68/04 | (2009.01) | |
| H04B 13/00 | (2006.01) | |
| H04N 5/232 | (2006.01) | |
| G01S 19/49 | (2010.01) | |
| G01P 1/12 | (2006.01) | |
| A61B 5/00 | (2006.01) | |
| A61B 5/11 | (2006.01) | |
| H04W 88/02 | (2009.01) | |
| H04N 5/91 | (2006.01) | |
| A61B 5/0205 | (2006.01) | |
| A61B 5/024 | (2006.01) | |
| H04N 21/442 | (2011.01) | |

(52) U.S. Cl.
CPC ............ *A61B 5/6895* (2013.01); *G01P 1/127* (2013.01); *G01S 19/49* (2013.01); *H04B 5/00* (2013.01); *H04B 5/0031* (2013.01); *H04B 13/005* (2013.01); *H04N 5/232* (2013.01); *H04N 5/23206* (2013.01); *H04W 68/04* (2013.01); *A61B 5/02055* (2013.01); *A61B 5/02416* (2013.01); *A61B 2562/0247* (2013.01); *H04N 5/91* (2013.01); *H04N 21/44218* (2013.01); *H04W 88/02* (2013.01)

(56) References Cited

U.S. PATENT DOCUMENTS

| | | | |
|---|---|---|---|
| 2009/0131188 A1 | 5/2009 | Choi | |
| 2010/0216564 A1 | 8/2010 | Stites et al. | |
| 2010/0323805 A1 | 12/2010 | Kamino et al. | |
| 2011/0299729 A1* | 12/2011 | Dawe ................ | A63B 24/0003 382/103 |
| 2012/0052971 A1* | 3/2012 | Bentley .............. | A63B 24/0006 473/222 |

FOREIGN PATENT DOCUMENTS

| | | |
|---|---|---|
| JP | H10-43348 A | 2/1998 |
| JP | 2001-078973 A | 3/2001 |
| JP | 2002-300651 A | 10/2002 |
| JP | 2004-065803 A | 3/2004 |
| JP | 2004-084406 A | 3/2004 |
| JP | 2005-082088 A | 3/2005 |
| JP | 2005-102902 A | 4/2005 |
| JP | 2005-110850 | 4/2005 |
| JP | 2005-152321 | 6/2005 |
| JP | 2005-270543 A | 10/2005 |
| JP | 2006-338336 A | 12/2006 |
| JP | 2007-033713 A | 2/2007 |
| JP | 2007-034911 A | 2/2007 |
| JP | 2007-530151 A | 11/2007 |
| JP | 2008-073210 A | 4/2008 |
| JP | 2008-286771 A | 11/2008 |
| JP | 2009-018026 A | 1/2009 |
| JP | 2009-172052 A | 8/2009 |
| JP | 2009-297240 A | 12/2009 |
| JP | 2010-039789 A | 2/2010 |
| JP | 2010-063863 A | 3/2010 |
| JP | 2010-125253 A | 6/2010 |
| JP | 2010191540 A | 9/2010 |
| JP | 2010-220631 A | 10/2010 |
| JP | 2011-000210 A | 1/2011 |
| JP | 2011-000425 A | 1/2011 |
| JP | 2011-502691 A | 1/2011 |
| WO | 2005/094953 A2 | 10/2005 |

OTHER PUBLICATIONS

Mar. 1, 2016 Office Action issued in Japanese Patent Application No. 2015-148136.
Mar. 1, 2016 Office Action issued in Japanese Patent Application No. 2015-122341.
Mar. 1, 2016 Office Action issued in Japanese Patent Application No. 2015-030003.
May 26, 2015 Office Action issued in Japanese Patent Application No. 2011-271542.
May 26, 2015 Office Action issued in Japanese Patent Application No. 2011-271543.
May 26, 2015 Office Action issued in Japanese Patent Application No. 2011-271544.
Aug. 18, 2015 Office Action issued in Japanese Patent Application No. 2011-271544.
Jan. 6, 2015 Office Action issued in Japanese Patent Application No. 2014-123513.
Dec. 4, 2012 Search Report issued in International Patent Application No. PCT/JP2012/079254.
Aug. 12, 2014 Office Action issued in Japanese Patent Application No. 2014-123513.
Itagaki, Yuuta. "Optimum Design of a Golf Club in Consideration of the Variability of Swing Motion". UTokyo Repository, Mar. 24, 2011, The University of Tokyo, Japan, pp. 1-4.
Mar. 29, 2016 Office Action issued in Japanese Patent Application No. 2011-271544.
Nov. 7, 2016 Office Action issued in Russian Patent Application No. 2014123710.
Dec. 15, 2016 Office Action issued in Chinese Application No. 201410392463.7.
Jan. 5, 2017 Office Action issued in Chinese Application No. 201280059292.5.
Dec. 20, 2016 Office Action issued in Japanese Application No. 2015-148136.
Dec. 20, 2016 Office Action issued in Japanese Application No. 2015-122341.
Dec. 20, 2016 Office Action issued in Japanese Application No. 2015-030003.
Jul. 19, 2016 Office Action issued in Japanese Application No. 2015-122341.
Jul. 19, 2016 Office Action issued in Japanese Application No. 2015-148136.
Jul. 19, 2016 Office Action issued in Japanese Application No. 2015-030003.
Wang, Chun Xiao, "Optimal design of golf club considering dispersion of swing", Optimal Symposium lecture dissertations, the ninth period, Dec. 9, 2010, pp. 15-18.
Jun. 17, 2016 Office Action issued in Chinese Application No. 201280059292.5.
Chinese Office Action dated Aug. 22, 2017 in corresponding Chinese Patent Application No. 201610232482.2.
Russian Office Action dated Jun. 21, 2017 in corresponding Russian Patent Application No. 2014123710/007(038646).
Japanese Office Action dated Mar. 6, 2018 in corresponding Japanese Patent Application No. 2017-055103.
Japanese Office Action dated Mar. 6, 2018 in corresponding Japanese Patent Application No. 2017-055110.
Japanese Office Action dated Mar. 6, 2018 in corresponding Japanese Patent Application No. 2017-055118.

* cited by examiner

FIG. 3A

<PRACTICE PLACE TABLE>

| USER ID | PRACTICE PLACE 1 | PRACTICE PLACE 2 | ... |
|---|---|---|---|
| 001 | A SCHOOL<br>1(NORTH LATITUDE:.., EAST LONGITUDE*..)<br>2(NORTH LATITUDE:.., EAST LONGITUDE*..)<br>3(NORTH LATITUDE:.., EAST LONGITUDE*..)<br>4(NORTH LATITUDE:.., EAST LONGITUDE*..) | B BASEBALL STADIUM<br>1(NORTH LATITUDE:.., EAST LONGITUDE*..)<br>2(NORTH LATITUDE:.., EAST LONGITUDE*..)<br>3(NORTH LATITUDE:.., EAST LONGITUDE*..)<br>4(NORTH LATITUDE:.., EAST LONGITUDE*..) | ... |

FIG. 3B

<PRACTICE DURATION DB>

| USER ID | PRACTICE ID | STARTING DATE AND TIME | FINISHING DATE AND TIME | PRACTICE DURATION |
|---|---|---|---|---|
| 001 | A.001 | 2011/12/12 16:30:00 | 2011/12/12 18:00:35 | 01:30:35 |
| 001 | A.002 | 2011/12/13 16:25:30 | | |

FIG. 3C

<SWING-PRACTICE DURATION DB>

| USER ID | PRACTICE ID | SWING STARTING DATE AND TIME | SWING FINISHING DATE AND TIME | PRACTICE DURATION |
|---|---|---|---|---|
| 001 | A.001 | 2011/12/12 16:45:00 | 2011/12/12 17:15:30 | 00:30:30 |
| 001 | A.002 | 2011/12/13 16:50:00 | | |

FIG. 4A

<SWING JUDGMENT TABLE>

| TYPE OF EQUIPMENT | ACCELERATION OUTPUT | ANGULAR VELOCITY OUTPUT |
|---|---|---|
| α | a1~a2 | b1~b2 |
| β | c1~c2 | d1~d2 |
| ⋮ | ⋮ | ⋮ |

FIG. 4B

<IMAGE DB>

| USER ID | PRACTICE ID | IMAGE FILE NAME | SHOOTING STARTING DATE AND TIME | SHOOTING FINISHING DATE AND TIME |
|---|---|---|---|---|
| 001 | A001 | A001.mp4 | 2011/12/12 16:45:00 | 2011/12/12 17:15:30 |
| 001 | A002 | A002.mp4 | 2011/12/13 16:50:00 | |

FIG. 5

<PRACTICE DATA DB>

| USER ID | PRACTICE ID | DATE AND TIME | TYPE OF EQUIP-MENT | ACCEL-ERATION SENSOR 11 | GYRO SENSOR 12 | BIO-SENSOR 13 | ACCEL-ERATION SENSOR 23b | NUMBER COUNTER |
|---|---|---|---|---|---|---|---|---|
| 001 | A001 | 2011/12/12 16:45:00 | α | *** | *** | *** | *** | 1 |
| 001 | A001 | 2011/12/12 16:45:15 | α | *** | *** | *** | *** | 2 |
| ... | ... | ... | ... | ... | ... | ... | ... | ... |
| 001 | A001 | 2011/12/12 17:13:50 | α | *** | *** | *** | *** | 185 |
| 001 | A002 | 2011/12/13 16:50:00 | α | *** | *** | *** | *** | 1 |

FIG. 9A
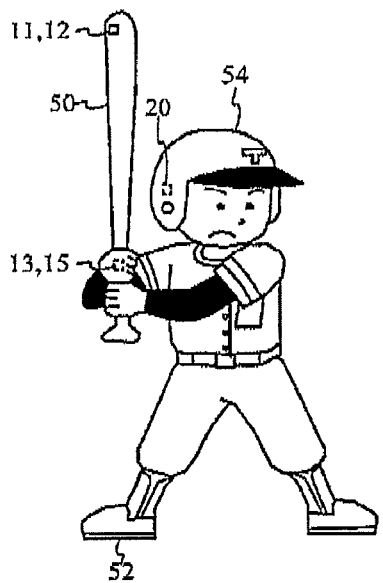
FIG. 9B
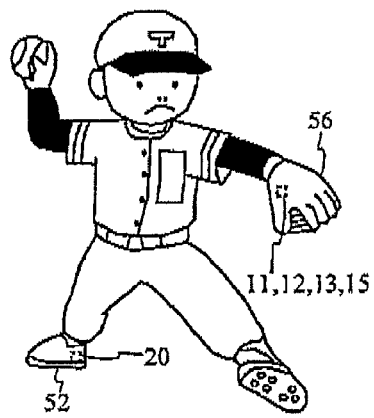
FIG. 9C
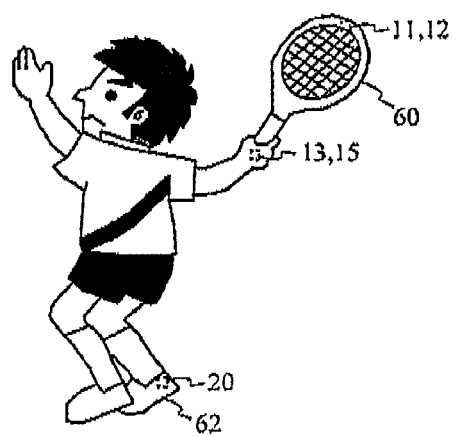

ELECTRONIC DEVICE

This is a continuation application of U.S. patent application Ser. No. 14/361,614 filed on May 29, 2014, which in turn is a National Phase application of International Application No. PCT/JP2012/079254 filed on Nov. 12, 2012, which in turn claims priority to Japanese Application No. 2011-271544 filed on Dec. 12, 2011, Japanese Application No. 2011-271543 filed on Dec. 12, 2011, and Japanese Application No. 2011-271542 filed on Dec. 12, 2011. The prior applications are incorporated herein by reference in their entirety.

TECHNICAL FIELD

The present invention relates to electronic devices.

BACKGROUND ART

There has been conventionally suggested a system storing a history of activities in daily life.

In recent years, there has been suggested storing an action history associated with locations by using intra-body communication (see Patent Document 1, for example).

PRIOR ART DOCUMENTS

Patent Documents

Patent Document 1: Japanese Patent Application Publication No. 2010-39789

SUMMARY OF THE INVENTION

Problems to be Solved by the Invention

However, the conventional system storing the action history has limitation in application thereof, and is not sufficiently convenient because the application to various scenes is not considered.

The present invention has been made in view of the above problems, and aims to provide a convenient electronic device.

Means for Solving the Problems

The electronic device of the present invention includes: a first communication unit located near a user; a receive unit configured to receive data through communication via a body of the user or near field communication between a second communication unit located in a member used by the user and the first communication unit; a recording unit configured to record data pertaining to the member when communication is established between the first communication unit and the second communication unit.

In the above case, the recording unit may record data pertaining to a member provided with the first communication unit. Additionally, the recording unit may record biological information of the user. Additionally, the recording unit may record data depending on an attribute of the member as the data pertaining to the member. Furthermore, the recording unit may record data depending on an attribute of a member provided with the second communication unit and a type of the member provided with the second communication unit as data pertaining to the member provided with the second communication unit.

The electronic device of the present invention may include a position detecting unit configured to detect a position, and the recording unit may record a position detected by the position detecting unit. Additionally, the recording unit may record duration of communication between the first communication unit and the second communication unit.

In the electronic device of the present invention, the first communication unit may include a first member capable of making contact with or facing a first part of a human body, and the second communication unit may include a second member capable of making contact with or facing a second part of the human body different from the first part. In the above case, the recording unit may record data pertaining to a movement of at least one of the first part and the second part. Additionally, the recording unit may finish recording data pertaining to the member provided with the second communication unit when the second member fails to make contact with or face the second member for a predetermined period of time. Additionally, the recording unit may finish recording the data when the first member stops making contact with or facing the first part.

The electronic device of the present invention may include a display unit displaying data recorded in chronological order by the recording unit.

The electronic device of the present invention includes: a first communication unit including a first member capable of making contact with or facing a first part of a human body; a receive unit configured to receive data through communication via the human body between a second communication unit and the first communication unit, the second communication unit including a second member capable of making contact with or facing a second part different from the first part; and a third communication unit different from the first communication unit.

In the above case, the third communication unit may communicate with an external device when communication via the human body is established between the first communication unit and the second communication unit, the external device failing to make contact with the human body. In the above case, the third communication unit may request the external device to record data pertaining to the human body. In the above case, a position detecting unit configured to detect a position may be included, and the third communication unit may request the external device to record data depending on a position detected by the position detecting unit. Additionally, the third communication unit may request the external device to finish recording the data when the second member fails to make contact with or face the second part for a predetermined period of time. Additionally, the third communication unit may request the external device to finish recording the data when the first member fails to make contact with or face the first part.

In the electronic device of the present invention, the external device may include an image capturing device, and the third communication unit may request the image capturing device to capture an image. In the above case, the third communication unit may receive a position of the image capturing device and make a request of capturing an image according to the position of the image capturing device.

In the electronic device of the present invention, the external device may include a memory device, and the third communication unit may request the memory device to store data received by the receive unit.

The electronic device of the present invention includes: a communication member located in a predetermined member and detecting a state of making contact with or facing a human body; a physical quantity sensor located in the predetermined member and detecting a physical quantity affecting the predetermined member according to a movement of the human body, and a communication unit configured to communicate the physical quantity detected by the physical quantity sensor with a different device from the predetermined member via the communication member and the human body.

In the above case, a biosensor detecting biological information of the human body may be provided in a location near a location in which the communication member of the predetermined member is located. In the above case, the communication member may include a first electrode making contact with or facing the human body, and the biosensor may include a second electrode making contact with or facing the human body. In the above case, a part of the first electrode may be shared with a part of the second electrode. Additionally, the communication unit may communicate the biological information together with the physical quantity with the different device.

The electronic device of the present invention may include a storage unit storing information about the predetermined member. In the above case, the communication unit may communicate the information about the predetermined member together with the physical quantity with the different device.

Additionally, in the electronic device of the present invention, the physical quantity sensor may include at least one of an acceleration sensor and an angular velocity sensor. Additionally, a control unit configured to control a detection timing of the physical quantity sensor may be included, and the control unit may start detecting the physical quantity with the physical quantity sensor after communication via the communication member and the human body is established between the communication unit and the different device.

Effects of the Invention

The present invention has an advantage in providing a convenient electronic device.

BRIEF DESCRIPTION OF DRAWINGS

FIG. 3A is a diagram illustrating a practice place table, FIG. 3B is a diagram illustrating a practice duration DB, and FIG. 3C is a diagram illustrating a swing-practice duration DB;

FIG. 4A is a diagram illustrating a swing judgment table, and FIG. 4B is a diagram illustrating an image DB;

FIG. 5 is a diagram illustrating a practice data DB;

FIG. 9A illustrates a case where the communication module is located in a baseball helmet (a first variation of the embodiment), FIG. 9B illustrates a case where the electronic device system is used when a user takes to the field in baseball (the first variation of the embodiment), and FIG. 9C illustrates a case where the electronic device system is used when the user plays tennis (a second variation of the embodiment)

MODES FOR CARRYING OUT THE INVENTION

Figure 1:
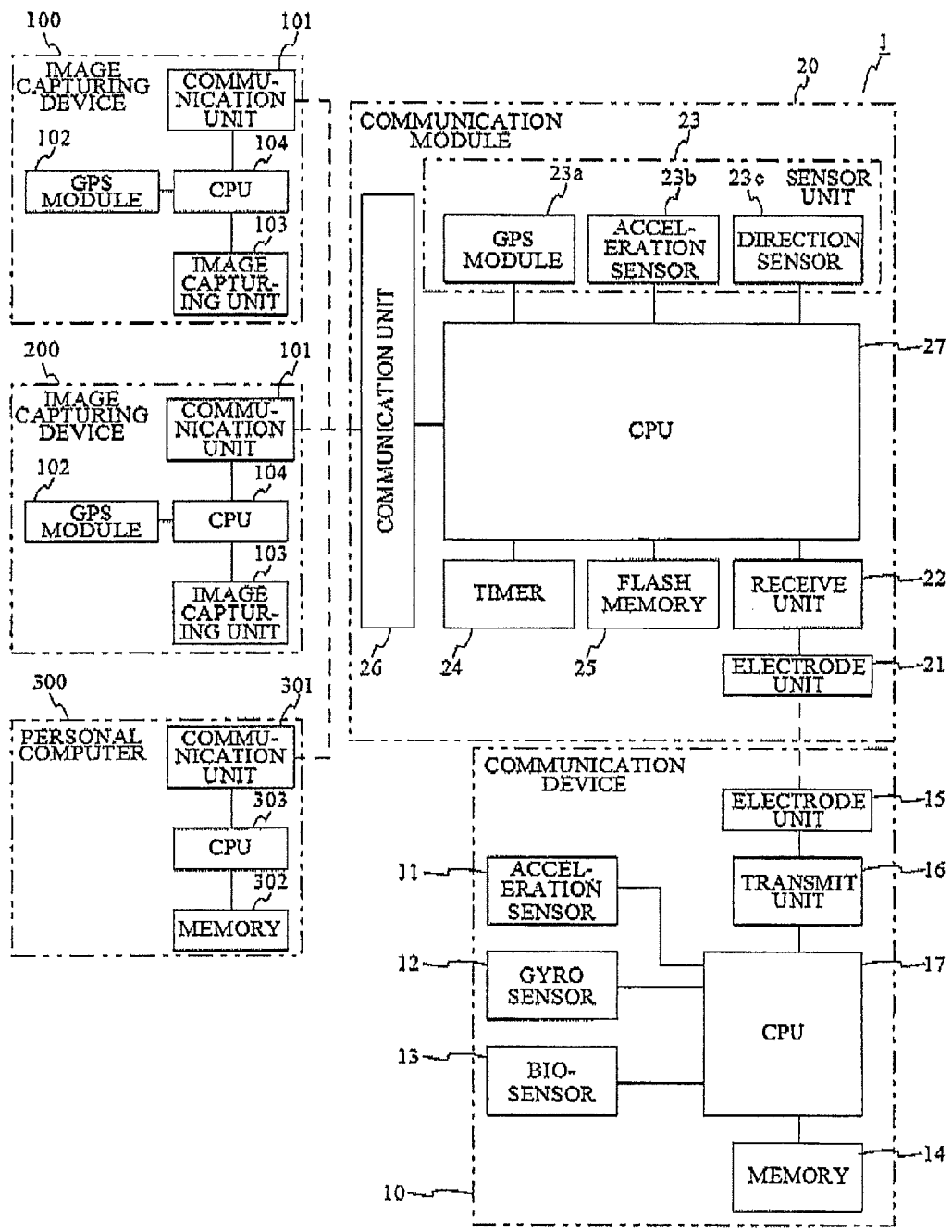
FIG. 1 is a block diagram illustrating a configuration of an electronic device system 1 in accordance with an exemplary embodiment.

Hereinafter, a description will be given of an electronic device system 1 in accordance with an exemplary embodiment with reference to FIG. 1 through FIG. 8. FIG. 1 is a block diagram illustrating a configuration of the electronic device system 1 in accordance with the present embodiment.

As illustrated in FIG. 1, the electronic device system 1 includes: a communication device 10 provided in equipment used when a user does activities such as sports; a communication module 20 communicating with the communication device 10; image capturing devices 100, 200 and a personal computer (hereinafter, referred to as a PC) 300 communicating with the communication module 20.

In the present embodiment, the communication device 10 communicates with the communication module 20 through intra-body communication using a human body, which is a conductor, as a signal transmission medium. There are some methods for intra-body communication including an electric current method that passes a minute electric current through a human body and modulates the electric current to transmit information and an electric field method that modulates an electric field induced on the surface of a human body to transmit information. In the present embodiment, any of the electric current method and the electric field method can be used. However, a description hereinafter will describe a case using intra-body communication of the electric field method.

(Communication Device 10)

The communication device 10 can be located in a helmet, a glove, a mitt, or a bat when the equipment is, for example, baseball equipment. In the present embodiment, assume that the communication device 10 is located in a bat 50 illustrated in FIG. 2.

The communication device 10 includes an acceleration sensor 11, a gyro sensor 12, a biosensor 13, a memory 14, an electrode unit 15, a transmit unit 16, and a CPU 17 as illustrated in FIG. 1.

The acceleration sensor 11 may employ a piezoelectric element or a strain gauge, and detects the acceleration of the bat 50. The number of axes of the acceleration sensor 11 may be arbitrarily selected from one through three, and the number of the acceleration sensors 11 may be arbitrarily determined.

The gyro sensor 12 detects a Coriolis force generated by the effect of angular velocity by using a piezoelectric element and detects the angular velocity of the bat 50 in the present embodiment. The number of axes of the gyro sensor 12 may be selected from one through three, and the number of the gyro sensor 12 may be arbitrarily determined.

In the present embodiment, the acceleration sensor 11 and the gyro sensor 12 are located in the bat 50. Thus, data such as the number of swings of and the swing speed of the bat 50 by the user can be acquired from the sensors and stored.

Figure 2:
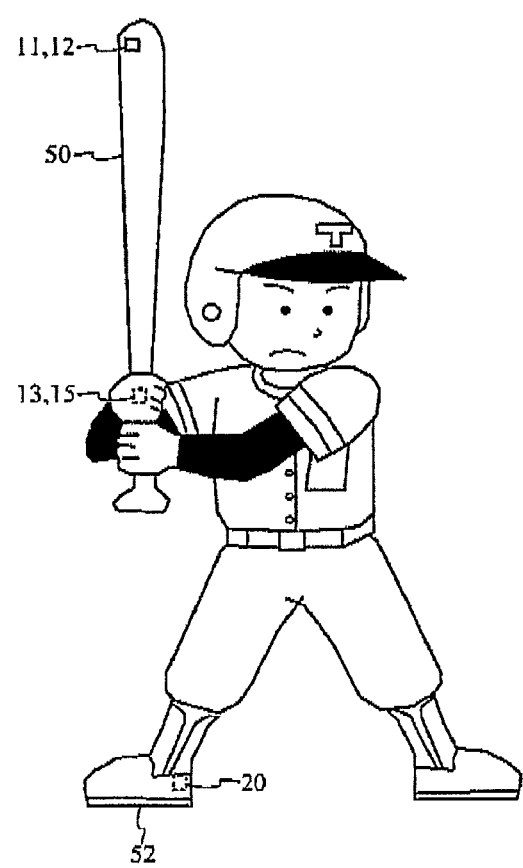
FIG. 2 is a diagram illustrating locations of a communication device and a communication module.

In the components of the communication device 10, the acceleration sensor 11 and the gyro sensor 12 are preferably located in the tip (head) of the bat 50 as illustrated in FIG. 2. In this case, assume that the acceleration sensor 11 and the gyro sensor 12 are located away from the biosensor 13 and the electrode unit 15 described later.

In addition, some of the components in the communication device 10 (the electrode unit 15 and the transmit unit 16, for example) may be configured to be detachable by attaching them to the bat 50 with an adhesive tape, and may be attached to another bat or another piece of equipment.

The biosensor 13 is located in a location (a grip) making contact with the user's hand in the bat 50 as illustrated in FIG. 2, and detects biological information of the user. The biosensor 13 includes a pulse sensor that irradiates a live body with an irradiation beam by an LED and receives a light beam reflected by the live body to detect a pulse, for example. Japanese Patent Application Publication No. 2005-270543 discloses an exemplary pulse sensor. A perspiration sensor in which electrodes are arranged may be employed as the biosensor 13 instead of or in addition to the pulse sensor. The use of the perspiration sensor makes it possible to detect the perspiration amount of the user. Furthermore, a temperature sensor measuring a body temperature or a blood pressure sensor measuring a blood pressure may be employed as the biosensor 13. The biosensor 13 is not limited to a sensor provided in the bat 50, and may be a watch-type biosensor disclosed in Japanese Patent Application Publication No. 2005-270543.

A pressure sensor located in the grip of the bat 50 may be employed as the biosensor 13. The electrode unit making up the biosensor 13 may be shared with the electrode unit 15, or separately provided.

The memory 14 is a nonvolatile memory (e.g. a flash memory) and stores information about the equipment. In the present embodiment, the memory 14 stores a type of the bat 50 (weight, length, material (metal or wood)).

The electrode unit 15 includes a signal electrode and a ground electrode, and is used to communicate with the communication module 20 via the user. The electrode unit 15 is located in a location making contact with the user's hand (the grip of the bat 50). Intra-body communication using the electrode unit 15 is performed not only when the user is barehanded (i.e. when the user's hand makes direct contact with the electrode unit 15) but also when the user wears gloves (i.e. when the user's hand faces the electrode unit 15).

When both the biosensor 13 and the electrode unit 15 are located in the location making contact with or facing a part of the body of the user (the hand in the present embodiment) in the bat, the biosensor 13 and the electrode unit 15 may be integrated into a single unit.

The transmit unit 16 includes an electrical circuit containing a bandpass filter, and transmits data stored in the memory 14 and detection results of the acceleration sensor 11, the gyro sensor 12, and the biosensor 13 to the communication module 20 via the electrode unit 15 and the human body.

The CPU 17 overall controls the communication device 10, and controls the data transmission to the communication module 20 in the present embodiment.

(Communication Module 20)

The communication module 20 receives data from the communication device 10 to collect data, and communicates with external devices (the image capturing devices 100, 200 and the PC 300) based on the received data.

The communication module 20 includes an electrode unit 21, a receive unit 22, a sensor unit 23, a timer 24, a flash memory 25, a communication unit 26, and a CPU 27.

The electrode unit 21 includes a signal electrode and a ground electrode, and is used for intra-body communication with the communication device 10 via the user. In the present embodiment, the electrode unit 21 is located in a location making contact with a foot of the user (the inside of a shoe (spike) 52 illustrated in FIG. 2). Intra-body communication can be performed not only when the user is barefoot (i.e. when the electrode unit 21 makes contact with the foot) but also when the user wears socks (i.e. when the electrode unit 21 faces the foot).

The receive unit 22 includes an electric circuit containing a bandpass filter, and receives various kinds of data transmitted from the communication device 10.

The sensor unit 23 includes a GPS module 23a, an acceleration sensor 23b, and a direction sensor 23c. The sensor unit 23 may include a biosensor acquiring biological information of the user in addition to the aforementioned components.

The GPS module 23a is a position detecting device that detects the position of the communication module 20. The positional information (the information about the position where the user exists) detected by the GPS module 23a is stored in the flash memory 25 described later.

The acceleration sensor 23b may employ a piezoelectric element or a strain gauge, and detects acceleration associated with the movement of the user's foot in the present embodiment. The number of axes of the acceleration sensor 23b may be arbitrarily selected from one through three, and the number of the acceleration sensors 23b may be arbitrarily determined.

The direction sensor 23c detects an azimuth direction, and detects an azimuth direction of geomagnetism from detection results of magnetic fields by a two-axis magnetic sensor detecting mutually orthogonal geomagnetic components.

The acceleration sensor 23b and the direction sensor 23c may be located in both shoes instead of one shoe (spike).

The timer 24 outputs duration for which the user is in a predetermined place and time information when the user takes a predetermined action (baseball practice or game) to the CPU 27.

The flash memory 25 is a nonvolatile memory, and stores various kinds of data transmitted from the communication device 10, various kinds of data detected by the sensor unit 23, and time information output from the timer 24. More specifically, the flash memory 25 stores a practice place table illustrated in FIG. 3A and a swing judgment table illustrated in FIG. 4A. In addition, the flash memory 25 stores a practice duration DB (database) illustrated in FIG. 3B, a swing-practice duration DB illustrated in FIG. 3C, and a practice data DB illustrated in FIG. 5 for storing various kinds of data. These tables and DBs are described in detail later.

The communication unit 26 communicates (e.g. bi-directionally communicates) with external devices (the image capturing devices 100, 200, the PC 300), and may perform communication over a radio, a wired line, or an electrical communication line. The communication unit 26 in the present embodiment requests the image capturing devices 100, 200 to capture images and transfers data to the PC 300 by a communication method other than intra-body communication. For example, the communication module 20 can identify the user by transmitting information for identifying the user (name or ID or height, weight, and sex) from the PC 300 to the communication unit 26 and storing the information for identifying the user in the flash memory 25. In the present embodiment, the communication module 20 is located in the shoe 52. The shoe 52 is not generally shared with other people, and thus is appropriate for identifying the user.

The CPU 27 controls the communication module 20, and overall controls the electronic device system 1. In the present embodiment, the CPU 27 controls recording data and detecting the change in the state of the user (a level of proficiency in baseball).

In the present embodiment, the electrode unit 21 is located in the shoe (spike) 52, but the components of the communication module 20 are integrated into a single unit and located in the shoe 52. The components of the communication module 20 may not be integrated into a single unit, and may be arbitrarily located in the shoe 52. The components other than the electrode unit 21 may be located in other than the shoe. In addition, the electrode unit 21 may be attached to clothes (a uniform) or a body with an adhesive tape.

(Image Capturing Devices 100, 200)

The image capturing devices 100, 200 are, for example, digital cameras, and may be the same digital cameras or different digital cameras. In the present embodiment, the image capturing devices 100, 200 have the same basic configuration, and thus a description will be given of the configuration of the image capturing device 100, and a description of the configuration of the image capturing device 200 is omitted.

The image capturing device 100 includes a communication unit 101, a GPS module 102, an image capturing unit 103, and a CPU 104.

The communication unit 101 communicates with the communication unit 26 of the communication module 20. The communication unit 101 receives an image capture request from the communication module 20. The communication unit 101 transmits the position of the image capturing device 100 and the specification of the image capturing device 100 to the communication module 20. The communication unit 101 is capable of communicating with the communication unit 301 of the PC 300, and transmits images captured by the image capturing unit 103 to the PC 300.

The GPS module 102 is a position detecting device that detects the position of the image capturing device 100, and the position of the image capturing device 100 is transmitted to the communication module 20 by the communication unit 101 as described previously.

The image capturing unit 103 includes lenses and an imaging element such as a CCD (Charge Coupled Device) image sensor or a CMOS (Complementary Metal Oxide Semiconductor) sensor, and shoots videos and still images.

The CPU 104 overall controls the image capturing device 100, and controls the timing to capture the image of the user (the start of image capturing and the end of image capturing) under the instruction from the communication module 20 in the present embodiment.

(PC 300)

The PC 300 includes a communication unit 301, a memory 302, and a CPU 303.

The communication unit 301 communicates with the communication unit 26 of the communication module 20, and receives various kinds of data from the communication module 20. The communication unit 301 receives data of images captured by the image capturing devices 100, 200.

The memory 302 is a nonvolatile a memory, and stores various kinds of data received from the communication module 20 and the image capturing devices 100, 200. The memory 302 stores an image DB illustrated in FIG. 4B. The image DB will be described in detail later.

The CPU 303 overall controls the PC 300, and records the user history (e.g. duration of baseball practice), judges the level of proficiency (e.g. increase in swing speed), and compares the user with a professional player or an advanced-level player in terms of a form or speed such as swing speed based on the various kinds of data received from the communication module 20 and the image capturing devices 100, 200.

A description will now be given of a process executed by the electronic device system 1 configured as described above with reference to FIG. 6.

Figure 6:
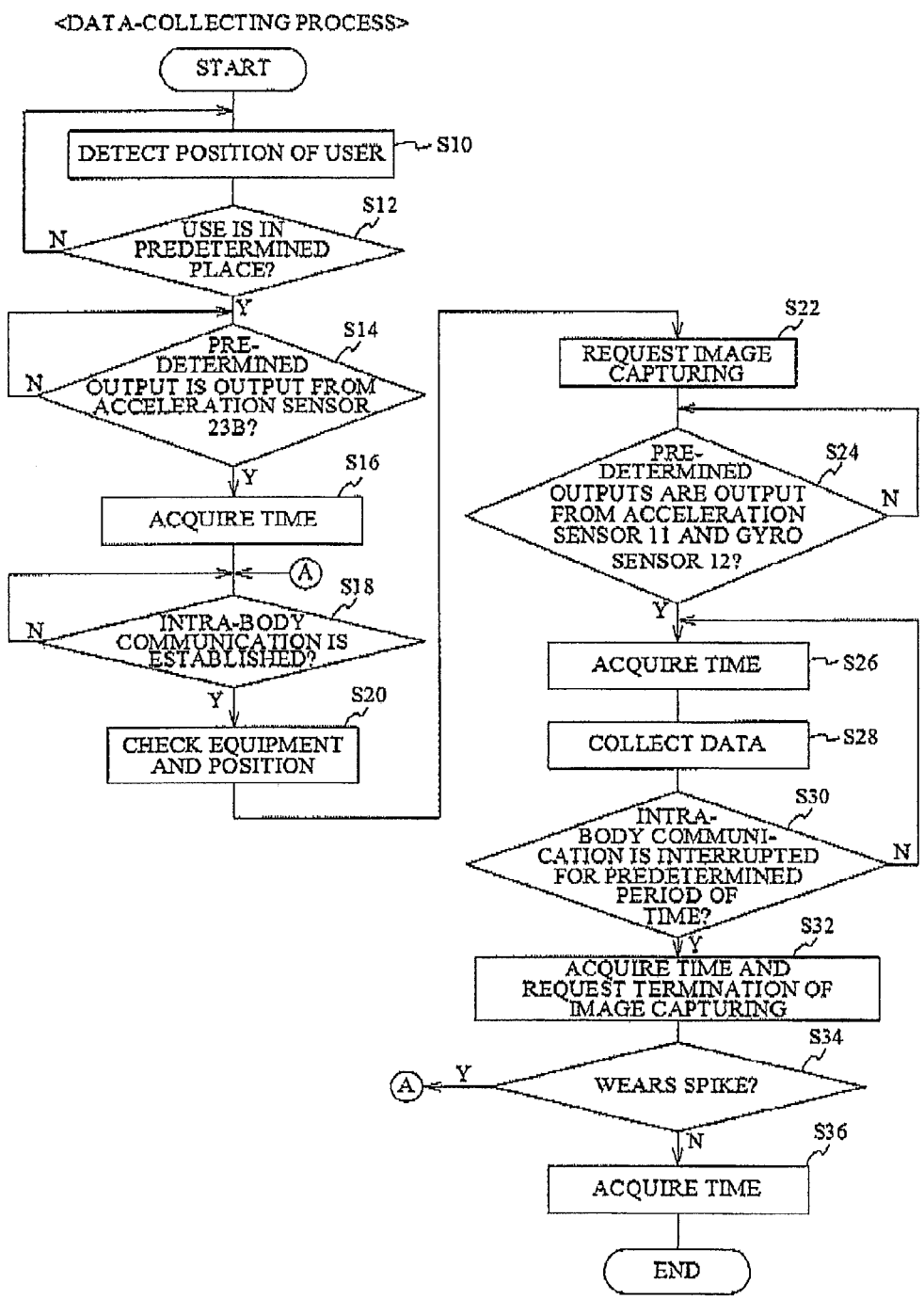
FIG. 6 is a flowchart illustrating a data-collecting process executed under the control by a CPU 27.

FIG. 6 is a flowchart of a data-collecting process executed under the control by the CPU 27. Assume that the process of FIG. 6 is started when the user puts on the shoe (spike) 52 provided with the electrode unit 21.

In the process of FIG. 6, at step S10, the CPU 27 acquires the output of the GPS module 23*a*, and detects the position of the user.

Then, at step S12, the CPU 27 determines whether the user is in a predetermined place based on the output of the GPS module 23*a*. Here, the predetermined place is a baseball stadium or a practice ground set by the user in advance. The predetermined place is stored in the practice place table illustrated in FIG. 3A. In FIG. 3A, the practice place is supposed to be a rectangle region, and is defined by latitudes and longitudes of the positions of four corners of the rectangle region. At step S12, when the output of the GPS module 23*a* is included in any of the regions of the practice places 1, 2 . . . stored in the practice place table, the determination becomes YES, and the process moves to step S14. When the determination at step S12 is NO, the process goes back to step S10.

Moving to step S14, the CPU 27 determines whether the acceleration sensor 23*b* outputs a predetermined output. Step S14 is a step for detecting the starting time of the practice of the user. The user usually warms up or runs before starting the practice with equipment in every sport, and thus the CPU 27 determines that the predetermined output is output when detecting acceleration different from acceleration in normal walking from the acceleration sensor 23*b* in the present embodiment. The acceleration in normal walking is set in advance. Therefore, when the walking user starts running, the determination at step S14 becomes YES, and the process moves to step S16.

At step S16, the CPU 27 acquires the date and time (time) information when the user starts warming-up exercise such as running from the timer 24. Step S16 is a step for recording the practice duration of the user. The date and time (time) information acquired at step S16 is input to a starting date and time field in the practice duration DB of FIG. 3B stored in the flash memory 25. When an entry is input to the starting time and date field of the practice duration DB, a serial number is input to a practice ID field.

As described above, the electronic device system 1 (the communication module 20) of the present embodiment automatically recognizes the start of the practice and automatically starts measuring the practice duration based on the user's act of putting on the shoe (spike) 52 and starting running, and therefore eliminates the need for the user to perform a particular operation to record the practice duration.

Then, at step S18, the CPU 27 determines whether intra-body communication is established between the electrode unit 21 located in the shoe (spike) 52 and the electrode unit 15 located in the bat 50. Here, when the user grips the bat 50 after warming up, intra-body communication is established between the electrode units 21 and 15. Thus, when the user grips the bat 50, the determination at step S18 becomes YES, and the process moves to step S20.

At step S20, the CPU 27 requests the communication device 10 located in the bat 50 to transmit information and acquires information about the position of the user from the GPS module 23a. The information of which the transmission is requested by the CPU 27 at step S20 includes information about a type of the bat (ID or data such as length, weight, and material) stored in the memory 14. In the communication device 10, the CPU 17 transmits the information about the type of the bat through the transmit unit 16.

Then, at step S22, the CPU 27 requests the image capturing devices 100, 200 to capture images based on the information about the position of the user detected at step S20.

For example, when the image capturing devices 100, 200 are fixed-point cameras, the CPU 27 transmits an image capture request to the image capturing device capable of capturing images of the user best, or requests the image capturing device 100 to capture images of the user from the front of the user and requests the image capturing device 200 to capture images from the side or the back of the user.

In addition, when requesting a cameraperson to capture images, the CPU 27 may inform the image capturing devices 100, 200 of the cameraperson of the position of the user. A mobile phone (a telephone function or a mail function) of the cameraperson may be used as the means of communicating with the cameraperson.

At step S24, the CPU 27 determines whether the acceleration sensor 11 and the gyro sensor 12 output predetermined outputs. Step S24 is a step for detecting whether the user starts swinging the bat 50, and the predetermined outputs are an acceleration value and an angular velocity value with which it can be determined that the user swings the bat 50. These values may be obtained from an experiment, or by analyzing the images of the swing. The values may be set with respect to each type of the bat. The information for determining the predetermined output of each sensor is defined, for example, in the swing judgment table illustrated in FIG. 4A.

The CPU 17 of the communication device 10 may start transmitting the outputs of the acceleration sensor 11 and the gyro sensor 12 to the communication module 20 when the acceleration sensor 11 and the gyro sensor 12 output the predetermined outputs after intra-body communication with the communication module 20 is established. Instead, the communication module 20 may request the communication device 10 to transmit the outputs of the acceleration sensor 11 and the gyro sensor 12 at predetermined intervals (e.g. every several tens of microseconds to every few seconds) after intra-body communication with the communication device 10 is established.

The execution order of step S22 and step S24 may be switched. In this case, the image capturing devices 100, 200 are requested to capture images after the swing of the bat 50 by the user is detected.

When the determination at step S24 is YES, the process moves to step S26, and the CPU 27 acquires the time when the user starts swinging the bat 50 from the timer 24. The acquisition of the time when the user starts swinging the bat 50 allows the CPU 27 to measure the duration for which the user swings the bat (batting practice duration) and calculate the ratio of the batting practice duration to the whole of the practice duration. The time acquired at step S24 is input to a swing starting date and time field in the swing-practice duration DB illustrated in FIG. 3C. As described above, the electronic device system 1 (the communication module 20) of the present embodiment automatically recognizes the batting practice and automatically starts measuring the batting practice duration based on the user's act of starting a swing. When inputting the time to the swing starting date and time field, the CPU 27 inputs the same string input to the practice ID field of the practice duration DB (see FIG. 3B) at step S16 to the practice ID field of the swing-practice duration DB.

Then, at step S28, the CPU 27 collects various kinds of data, and stores the collected data in the flash memory 25 (stores it in the practice data DB in FIG. 5). At this time, the CPU 27 records data depending on the way to use the equipment used by the user (attribute). In the present embodiment, the user uses the bat 50. Thus, the CPU 27 acquires the outputs of the acceleration sensor 11 and the gyro sensor 12 and the output of the biosensor 13 transmitted by the CPU 17 through the transmit unit 16 via the receive unit 22 and stores the acceleration (the detection value of the acceleration sensor 11), the angular velocity (the detection value of the gyro sensor 12), the biological information (the detection value of the biosensor 13), and the number of swings while the user swings the bat in the practice data DB. In addition, the CPU 27 collects the acceleration information (the detection value of the acceleration sensor 23b) associated with the movement of the foot when the user swings the bat from the acceleration sensor 23b. The results detected at step S24 may be used for the above-described data collection. The data stored in the practice data DB is not limited to data of each swing illustrated in FIG. 5, and the maximum acceleration, the average acceleration, the maximum angular velocity, and the average angular velocity of multiple swings or the maximum acceleration and the average acceleration associated with the movement of the foot may be stored in the practice data DB. In addition, the number of times that the acceleration exceeds the target acceleration may be stored. When storing the biological information, the CPU 27 may store the detection value (e.g. row data of a heart rate) of the biosensor 13 without change or may determine the state of the user (normal, tense, flaccid, relaxed) from the detection value of the biosensor 13 and store the determined state. In addition, the CPU 27 may store the detection values of the GPS module 23a and the direction sensor 23c in the practice data DB in FIG. 5. This makes it possible to analyze the practice data in consideration of the position of the user and the azimuth direction that the user faces.

The CPU 27 may store the collected data in the memory 302 of the PC 300 in addition to or instead of the flash memory 25.

The CPU 27 stores data about the swing in the practice data DB in association with the type of the equipment (the weight and the length of the bat) as illustrated in FIG. 5. This allows the practice data DB to store the attributes such as what and how equipment is used by the user. In addition, the CPU 27 counts the number of swings with respect to each practice ID in the practice data DB as illustrated in FIG. 5. This allows a comparison of the number of swings and the level of proficiency between practices.

Then, at step S30 of FIG. 6, the CPU 27 determines whether intra-body communication is interrupted for a predetermined period of time between the communication module 20 and the communication device 10. Step S30 is a step for checking whether the user continues the practice of swinging the bat 50 (batting practice). That is to say, when intra-body communication is interrupted for the predetermined period of time (e.g. for a few minutes), the CPU 27 determines that the user finished the batting practice. The predetermined period of time can be set with respect to each user. Instead of the above-described method, the CPU 27 may determine that the user finished the batting practice when intra-body communication with the communication device 10 provided in another piece of equipment (e.g. a glove) is established, or when determining that the user starts moving based on the output of the GPS module 23*a* or the direction sensor 23*c*.

While the determination at step S30 is NO, i.e. while intra-body communication is not interrupted for the predetermined period of time, the CPU 27 goes back to step S26, and repeats steps S26 and S28 to continue collecting the time information and various kinds of data.

On the other hand, when the determination at step S30 becomes YES, i.e. when intra-body communication is interrupted for the predetermined period of time, the CPU 27 checks the time through the timer 24 at step S32. Then, the CPU 27 calculates the batting practice duration from the checked time, and stores it in the swing-practice duration DB (a practice duration field of FIG. 3C) of the flash memory 25. As described above, the electronic device system 1 (the communication module 20) of the present embodiment automatically recognizes the end of the batting practice based on the fact that intra-body communication is interrupted for the predetermined period of time, and automatically finishes measuring the batting practice duration.

In addition, at step S32, the CPU 27 requests the image capturing devices 100, 200 to terminate capturing images. When the image capturing devices 100, 200 are fixed-point cameras and shoot videos, the video can be shot efficiently by transmitting the requests for starting and terminating the video shooting. This is effective especially when the video of each at-bat of the user is shot.

Then, at step S34, the CPU 27 determines whether the user wears the spike. The CPU 27 determines that the user will perform another practice and goes back to step S18 when the user keeps wearing the spike, but acquires the time information through the timer 24 at step S36 and stores data in the flash memory 25 (a finishing time field and a practice duration field of the practice duration DB (see FIG. 3B)) before ending the entire process of FIG. 6 when the user takes off the spike. When acquiring information about the finishing time of the practice at step S36, the CPU 27 may acquire the time when the user takes off the spike as the finishing time, or acquire the time when the predetermined output is lastly output from the acceleration sensor 23*b* (the output different from the output in walking) before the user takes off the spike as the finishing time.

At step S34, when it is necessary to set a predetermined period of time to determine whether the user does not wear the spike, a period of time less than the predetermined period of time set at step S30 may be set. In addition, the CPU 27 may determine whether to go back to step S18 in consideration of whether the user is in the practice ground. Step S34 may be executed before step S30, or step S34 may be executed before or after step S30. The determination whether the user wears the spike may be always executed separately from the process of FIG. 6, and the process of FIG. 6 may be force-quitted when the determination becomes NO.

As described above, the electronic device system 1 (the communication module 20) of the present embodiment automatically recognizes the end of the practice by using the user's act of taking off the spike as a trigger, and automatically finishes measuring the practice duration, and therefore eliminates the need to force the user to perform a particular operation.

A description will now be given of a data comparison process of the present embodiment executed under the control by the CPU 303 with reference to a flowchart of FIG. 7. The data comparison process is a process of comparing data between a target advanced-level person (e.g. a senior student or a professional player) and the user. Hereinafter, a description will be given under the assumption that the data (the practice data DB) collected through the process of FIG. 6 is transferred from the communication module 20 to the memory 302 of the PC 300.

Figure 7:
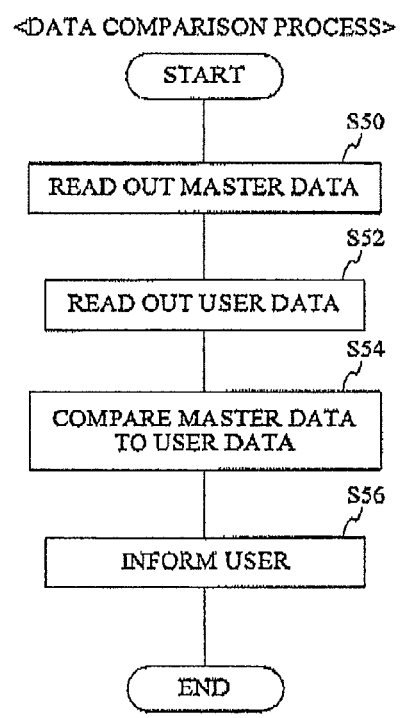
FIG. 7 is a flowchart illustrating a data comparison process executed under the control by a CPU 303.

At step S50 of FIG. 7, the CPU 303 reads out master data that the user targets on. At this time, the data selected by the user may be read out from the data of players (e.g. senior students) collected through the process of the flowchart of FIG. 6 as the master data. That is to say, the master data may be selected from the data stored in the memory 302. Or, target values such as swing speed and acceleration input to the PC 300 by the user in advance may be read out from the memory 302. Or, data of a professional player may be stored in the memory 302 in advance, and the CPU 303 may read out the data of the professional player.

Then, at step S52, the CPU 303 reads out the data of the user. In the present embodiment, the data of the user collected through the process described in the flowchart of FIG. 6 is read out from the memory 302.

At step S54, the CPU 303 compares the master data to the user data. In this case, the CPU 303 compares the master data to the time series variation (transition) of the user data to determine whether the user data becomes closer to the master data. For example, as illustrated in FIG. 8, the swing data of the professional player may be compared to the swing data of the user (e.g. the swing speed (maximum value) of each date).

Then, at step S56, the CPU 303 inform the user of the comparison result by displaying the comparison result of step S54 (FIG. 8) on an unillustrated display of the PC 300, and ends the entire process of FIG. 7. At step S56, the CPU 303 may display (report) the progress of the amount of the practice of the user (the number of swings and the practice duration) together as illustrated in FIG. 8.

Figure 8:
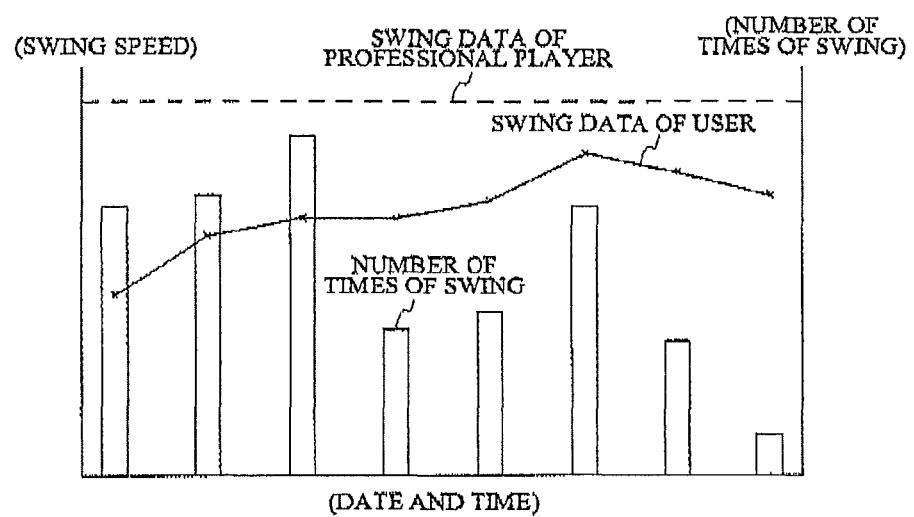
FIG. 8 is a diagram illustrating comparison results at step S54 in FIG. 7.

FIG. 8 is an exemplary example. That is to say, the CPU 303 may perform various analyses based on the practice data DB of FIG. 5, and inform the user of them. For example, when it can be determined whether the practice ID represents practice or a game based on the input information from the user, the difference in swing or mental state (the state based on the detection value of the biosensor 13) between the practice and the game is identified and reported to the user. In the flowchart of FIG. 7, the master data is compared to the user data. Instead, the practice amount may be set by the PC 300 and the user data may be compared to the set practice amount.

Collective management of data collected from users in the PC 300 allows a manager or a coach to recognize the state of the practice of each user (e.g. the state that the batting practice duration is long but the duration of other practice is short) or a user (player) who feels nervous or loses mental stability in a game, and helps the manager or the coach to set the practice amount, the order of practice, and a practice method.

As described above, in the present embodiment, the CPU 27 stores data depending on an attribute of a member (the bat 50) provided with the communication device 10 in the flash memory 25 (the practice data DB) when communication via a human body is established between the communication module 20 and the communication device 10 while the electrode unit 21 of the communication module 20 makes contact with or faces the foot of the user and the electrode unit 15 of the communication device 10 makes contact with or faces the hand of the user. Therefore, in the present embodiment, the recordation of data depending on the attribute of the member (the number of swings and the swing speed) is started when intra-body communication is established. This makes it possible to record data depending on the attribute of the member at an appropriate timing when the user grips the bat and starts the practice. This allows the provision of an convenient electronic device system.

Additionally, in the present embodiment, the CPU 27 stores data depending on the attribute of the shoe (spike) (acceleration and speed) in the flash memory 25 (the practice data DB), and therefore, the state of the practice is recorded from various perspectives.

Additionally, in the present embodiment, the CPU 27 stores biological information of the human body in the flash memory 25 (the practice data DB). Therefore, data such as the state of the practice and the difference in mental state between practice and a game is recorded from various perspectives.

Additionally, in the present embodiment, the CPU 27 also stores the type of the member (the type of the bat) in the flash memory 25 (the practice data DB), and thus, data such as what and how equipment (bat) is used by the user can be recorded.

Additionally, the CPU 27 stores the duration for which intra-body communication is performed in the flash memory 25 (the swing-practice duration DB), and thus, the duration for which the swing practice using the bat is performed can be recorded.

Additionally, the CPU 27 finishes recording the data depending on the attribute of the equipment (the bat) when the electrode unit 15 fails to make contact with or face the hand for a predetermined period of time (when intra-body communication is interrupted for a predetermined period of time) (step S30/YES). Therefore, the recordation of the practice data can be terminated at an appropriate timing when the probability that the practice using the bat is recessed or stopped is high.

Additionally, the CPU 27 finishes recording the data (inputs the finishing date and time to the practice duration DB) when the electrode unit 21 stops making contact with or facing the foot (when the user takes off the spike 52) (S34: NO). Therefore, the recordation can be terminated (the finishing date and time is input to the practice duration DB) at an appropriate timing when the probability that the user finishes the practice is high.

Additionally, in the present embodiment, the communication module 20 includes the communication unit 26 different from the communication unit (including the electrode unit 21 and the CPU 27) performing intra-body communication. This allows the communication unit 26 to perform communication based on the data received by the receive unit 22 of the communication module 20 from the communication device 10 through intra-body communication or the receive timing. In the present embodiment, the communication unit 26 communicates with the image capturing devices 100, 200 when intra-body communication through the electrode units 15, 21 is established. This makes it possible to request the image capturing devices 100, 200 to capture images at an appropriate timing such as the timing when the user starts the swing practice.

Additionally, in the present embodiment, the CPU 27 can requests the image capturing devices 100, 200 to capture images based on the position detected by the GPS module 23a. This makes it possible to request the image capturing devices 100, 200 to capture appropriate images of the user.

In addition, the CPU 27 requests the image capturing devices 100, 200 to terminate capturing images (S32) when the bat fails to make contact with or face the hand of the user for a predetermined period of time. Therefore, the image capturing can be terminated at an appropriate timing when the probability that the user finishes the swing practice is high.

Additionally, in the present embodiment, physical quantity sensors (the acceleration sensor 11 and the gyro sensor 12) detecting the physical quantity (acceleration and angular velocity) affecting the bat according to the movement of the user are located in the bat 50, and the CPU 17 and the transmit unit 16 communicate the physical quantity detected by the physical quantity sensor with a device (the communication module 20) different from the bat 50 via the electrode unit 15 making contact with or facing a human body and the human body. This makes it possible to transmit the physical quantity affecting the bat 50 to the communication module 20 through intra-body communication at an appropriate timing when the user grips the bat and starts the swing practice. From this point of view, it is possible to provide the convenient electronic device system 1.

In addition, in the present embodiment, the biosensor 13 is located near the electrode unit 15, and thus biological information detected by the biosensor 13 can be transmitted to the communication module 20 together with the physical quantity affecting the bat 50 according to the movement of the user at an appropriate timing.

In addition, in the present embodiment, the CPU 17 starts the detection by the acceleration sensor 11 and the gyro sensor 12 after intra-body communication is established, and thus the detection timing of each sensor can be made to be an appropriate timing. This reduces the power consumption of each sensor.

The above-described embodiment describes a case where images are captured by the image capturing devices 100, 200 during the swing practice, but does not intend to suggest any limitation. Images during the entire practice can be captured by the image capturing devices 100, 200. In this case, the CPU 27 executes step S22 of FIG. 6 immediately after step S16, and requests the termination of image capturing of step S32 immediately after step S34.

In the above-described embodiment, the acceleration sensor 11 and the gyro sensor 12 are located away from the biosensor 13 and the electrode unit 15. However, this does not intend to suggest any limitation, and the acceleration sensor 11 and the gyro sensor 12 may be located near the biosensor 13 and the electrode unit 15 (a knob, for example).

In the above-described embodiment, information about the type of equipment in the practice data DB may be used to manage the history of the period of use of the equipment. In addition, it may be used to recommend new equipment to the user according to the level of proficiency of the user.

In the above-described embodiment, the communication module 20 is located in a shoe, but the electrode unit may be located in a mobile terminal such as a mobile phone and the mobile terminal may be used as the communication module 20. In this case, the comparison result may be displayed on the screen (display) of the mobile terminal. When the information for identifying the user is stored in the mobile terminal, the above-described step of identifying the user by using the PC 300 can be omitted. In addition, input of the order of the practice and the practice amount from the input unit of the mobile terminal allows a comparison of the scheduled practice with the practice actually done. In this case, the comparison result may be displayed on the screen of the mobile terminal. In addition, when the scheduled practice amount is achieved, the user may be informed of that by a vibration function of the mobile terminal. The order of the practice and the practice amount may be transmitted from the PC 300 to the communication module 20 and stored in the flash memory 25.

The above-described embodiment describes a case where the CPU 27 stores the practice data in the flash memory 25 during the swing practice of the user, but does not intend to suggest any limitation. The CPU 27 may request the PC 300 to store the practice data when the user starts the swing practice.

Additionally, the above-described embodiment describes a case where the practice data is stored only when the user is in the predetermined place at step S12 of FIG. 6, but does not intend to suggest any limitation. For example, steps S10, S12 of FIG. 6 may be omitted, and the process of FIG. 6 may be started from step S14. In addition, in the process of FIG. 6, steps S14 and S16 are executed in consideration of warming-up exercise. However, this does not intend to suggest any limitation, and steps S14, S16 may be omitted from the process of FIG. 6, and the process of FIG. 6 may be started from step S18. In this case, steps S34, S36 may be also omitted.

In the above-described embodiment, the process of FIG. 7 may be executed by the CPU 27 of the communication module 20 instead of the CPU 303. In this case, the PC 300 may be omitted.

First Variation of the Embodiment

The above-described embodiment describes a case where the communication module 20 is located in the spike 52, but does not intend to suggest any limitation. For example, as illustrated in FIG. 9A, the communication module 20 may be located in a helmet 54. In this case, the CPU 27 may forbid the user from stepping into the batter's box to ensure the safety of the user (batter) when intra-body communication is not established between the helmet 54 and the bat 50 by providing a loudspeaker to the communication device 10 and inform the user by using the loudspeaker.

When gaining a base, the user (batter) does not hold the bat 50, and thus the acceleration sensor 11, the gyro sensor 12, the biosensor 13, and the electrode unit 15 may be located in the helmet 54 to detect the movement of the user while the user is on base. In this case, the communication module 20 may be located in the spike 52 or the helmet 54.

As illustrated in FIG. 9B, when taking to the field, the user uses a glove 56, and thus the glove 56 may be provided with the acceleration sensor 11, the gyro sensor 12, the biosensor 13, and the electrode unit 15. In this case, data such as the number of times that the user receives a ball and the speed of the ball (strength of the impact received by the glove 56) may be stored. The use of these data makes it possible to determine that the user can gradually catch a strong ball (a high-speed ball). In addition, when the acceleration sensor 11 is located in a catcher mitt, the state of a pitcher may be analyzed from the strength of the ball thrown by the pitcher and the change in the strength.

When the user is a catcher, a part of the protector may be provided with the acceleration sensor 11, the gyro sensor 12, the biosensor 13, and the electrode unit 15 may be provided to.

When the acceleration sensor 11 is located in the glove 56 or the protector, the CPU 27 may acquire a type of the glove 56 such as an infield grove, an outfield glove, or a catcher mitt or a type of the protector from the communication device 10 at step S20 of FIG. 6. At step S28, the CPU 27 may store data including attributes such as what and how equipment is used by the user by storing the way to use the equipment in association with the type of the glove 56 in the flash memory 25 (the practice data DB).

Second Variation of the Embodiment

FIG. 9C illustrates a case where the electronic device system 1 is applied to tennis. In the second variation of the embodiment, the biosensor 13 and the electrode unit 15 are located in a grip portion of a racket 60 (a location making contact with the user's hand), and the acceleration sensor 11 and the gyro sensor 12 are located in the tip of the face of the racket 60. In addition, in the second variation of the embodiment, the communication module 20 is located in a tennis shoe 62. In the case of tennis, data such as the number of swings and the swing speed of the racket can be stored, and data about step patterns can be stored (step S28). The acceleration sensor 11 and the gyro sensor 12 may be located near the grip portion of the racket 60.

In the second variation of the embodiment, the position of a tennis court is stored in the practice place table of FIG. 3A.

Third Variation of the Embodiment

Figure 10A:
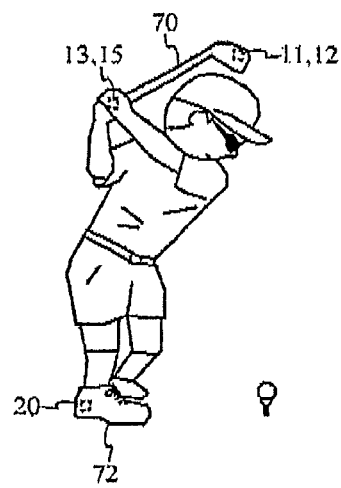
FIG. 10A illustrates a case where the electronic device system is used when the user plays golf (a third variation of the embodiment)

FIG. 10A illustrates a case where the electronic device system 1 is applied to golf. In the third variation of the embodiment, the biosensor 13 and the electrode unit 15 are located in the grip portion of a golf club 70, and the acceleration sensor 11 and the gyro sensor 12 are located in the clubhead. Additionally, the communication module 20 is located in a golf shoe 72. In this case, the CPU 27 acquires a type of the golf club 70 (club number, loft, lie angle, shaft, length, weight, material) from the communication device 10 at step S20 of FIG. 6. Then, at step S28, the CPU 27 stores data including attributes such as what and how equipment is used by the user by storing the way to use the equipment (the number of swings of the club, head speed, and use frequency of each club) in the flash memory 25 (the practice data DB) in association with the type of the golf club 70.

In the third variation of the embodiment, a golf course and a golf practice place are stored in the practice place table of FIG. 3A. In the golf course, the user is obliged to wear a hat or a sun visor, and thus the hat or the sun visor may be provided with the acceleration sensor 11, the gyro sensor 12, the biosensor 13, and the electrode unit 15, or the communication module 20. In addition, when pressure sensors are located on the face portion of the golf club, and the detection values of the pressure sensors of each shot are acquired, the contact position of the ball on the face can be stored for each shot.

Fourth Variation of the Embodiment

Figure 10B:
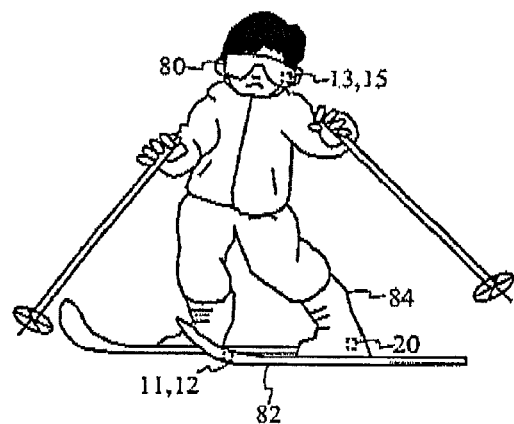
FIG. 10B illustrates a case where the electronic device system is used when the user skis (a fourth variation of the embodiment)

FIG. 10B illustrates a case where the electronic device system 1 is applied to ski. In the fourth variation of the embodiment, the biosensor 13 and the electrode unit 15 are located in a snow goggle 80, and the acceleration sensor 11 and the gyro sensor 12 are located in a ski 82. In addition, the communication module 20 is located in a ski shoe 84. In this case, the schuss speed of the user and the history of turns when the user makes a turn are stored. In addition, the provision of load sensors inside the ski shoe 84 makes it possible to store the change in the barycentric position of the user and the state of weight shift.

When skiing, the user is likely to move. In this case, the CPU 27 informs the image capturing devices 100, 200 of the moving direction of the user based on the output of the direction sensor 23c at step S22 of FIG. 6.

In addition, in skiing, the occurrence of emergency situation is expected when high acceleration affects the acceleration sensors 11, 23b, and then intra-body communication remains interrupted. In the above-described case, the CPU 27 may inform another external device (e.g. a mobile phone) of the occurrence of the emergency situation in addition to the positional information through the communication unit 26.

A stock may be equipped with the acceleration sensor 11 and the gyro sensor 12.

As with ski, the electronic device system 1 can be applied to snowboarding and skating.

Fifth Variation of the Embodiment

Figure 10C:
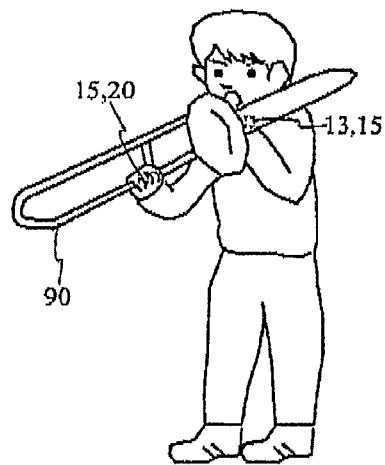
FIG. 10C illustrates a case where the electronic device system is used when the user plays an instrument (a trombone) (a fifth variation of the embodiment)

FIG. 10C illustrates a case where the electronic device system 1 is applied to performance of an instrument. In FIG. 10C, the biosensor 13, the electrode unit 15, and the communication module 20 are located in parts making contact with a right hand and a left hand so that intra-body communication is established when the user holds an instrument (trombone) 90 with both hands. When the player wears a shoe, the shoe may be provided with the communication module 20. At least one of or both the acceleration sensor 11 and the gyro sensor 12 may be provided or both may be omitted depending on the type of the instrument. In the case of the instrument, the data of the practice duration can be stored, and biological information during practice can be compared with biological information during a recital. In the fifth variation of the embodiment, the image capturing devices 100, 200 can capture images of the user while the user plays the instrument even when the user is in an orchestra. In the fifth variation of the embodiment, a recording device may be used as an external device controlled by the CPU 27 instead of or together with the image capturing devices 100, 200. When the performance of the orchestra is recorded with the recording device, the user may be informed of a point to be improved (off key from other players) by comparing the recorded sound data and the user's operation to the instrument (the movement of the user's right hand acquired from the acceleration sensor 11 (the movement of the slide tube)).

The electronic device system 1 may be applied to an instrument other than a trombone.

Sixth Variation of the Embodiment

Figure 10D:
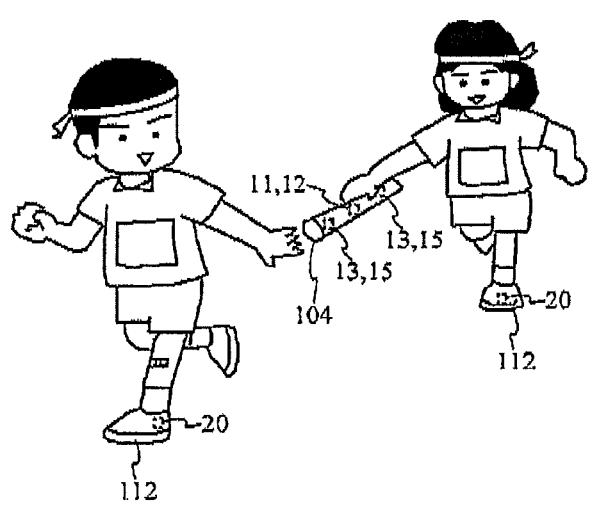
FIG. 10D illustrates a case where the electronic device system is used when the user plays athletic sports (a relay race) (a sixth variation of the embodiment).

FIG. 10D illustrates a case where the electronic device system 1 is applied to athletic sports (a relay race). In this case, the communication module 20 is located in each of shoes 112 of two runners, the biosensors 13 and the electrode units 15 are located in both ends of a baton 104, and the acceleration sensor 11 and the gyro sensor 12 are located in the baton 104. This configuration makes it possible to acquire the movement of the baton 104 during a relay race and the biological information of two runners, and thereby visualize the data of the benefit of preparation.

As with the ski, the user is likely to move in athletic sports. In such a case, the CPU 27 may inform the image capturing devices 100, 200 of the moving direction of the user based on the output of the direction sensor 23c at step S22 of FIG. 6.

In the above-described embodiment and the variations thereof, when the communication module 20 is located in a shoe, the sensor unit 23 may include a load sensor. This configuration makes it possible to detect the barycentric position and the body balance of the user, and thereby to analyze a point to be improved in the swing.

The electronic device system 1 can be applied to various sports using equipment other than baseball, tennis, golf, ski, and athletic sports, such as table tennis, badminton, hockey, Japanese art of fencing, fencing, boat, horse race (the communication device 10 is provided to a whip of a jockey), archery, lacrosse, and cricket.

The above-described embodiment describes a case where the communication device 10 communicates with the communication module 20 through intra-body communication, but does not intend to suggest any limitation. For example, the communication device 10 may communicate with the communication module 20 through near field communication. Even in this case, when the communication range of near field communication is set within the maximum distance that the human body can reach (distance from the tip of the finger of the outreached hand to the tip of the foot), the communication device 10 located in the shoe communicates with the communication module 20 located in the bat 50 at the timing when the user holds the equipment (e.g. the bat 50), and therefore the same effect as the above-described embodiment can be achieved.

While the exemplary embodiments of the present invention have been illustrated in detail, the present invention is not limited to the above-mentioned embodiments, and other embodiments, variations and modifications may be made without departing from the scope of the present invention. The entire disclosure of the publication cited in the above description is incorporated herein by reference.

What is claimed is:

1. A non-transitory computer readable medium storing a program causing a processor of a mobile terminal to execute a process, the mobile terminal including: a camera; a display; a memory; and the processor, the process comprising:
while communicating with a device including a sensor attached to equipment used to perform a swing, the device measuring acceleration and angular velocity of the device,
causing the camera to capture an image and
receiving, from the device, first data including acceleration and angular velocity of the device measured by the sensor attached to the equipment;
storing in the memory the first data including the acceleration and the angular velocity of the device measured by the sensor in association with image data generated by the camera;
reading second data relating to a second swing stored in the memory; and
displaying on the display (i) information based on the first data, (ii) information based on the second data in a comparable manner, and (iii) an associated image generated from the image data.

2. The non-transitory computer readable medium according to claim 1, wherein the process further comprises transmitting the information based on the first data to an external device.

3. The non-transitory computer readable medium according to claim 1, wherein the process further comprises extracting data of a maximum acceleration from a plurality of the data relating to the acceleration.

4. The non-transitory computer readable medium according to claim 1, wherein the process further comprises extracting data of a maximum angular velocity from a plurality of data relating to the angular velocity.

5. The non-transitory computer readable medium according to claim 1, wherein the process further comprises storing a body height of a user of the equipment in the memory.

6. The non-transitory computer readable medium according to claim 1, wherein the process further comprises storing a type of the equipment in the memory.

7. The non-transitory computer readable medium according to claim 1, wherein the process further comprises reading the second data specified from a plurality of the second data stored in the memory.

8. The non-transitory computer readable medium according to claim 1,
wherein
the process further comprises causing the mobile terminal to perform notification about the swing.

9. The non-transitory computer readable medium according to claim 1, wherein the storing includes storing in the memory the first data including the acceleration and the angular velocity measured by the sensor in association with the image data generated by the camera depending on the first data.

10. A non-transitory computer readable medium storing a program causing a processor of a mobile terminal to execute a process, the mobile terminal including: a camera configured to capture an image; a communication interface configured to communicate with an external device including a sensor attached to equipment, the external device measuring acceleration and angular velocity of the external device; a memory; and the processor, the process comprising:
capturing, by the camera, an image of a swing performed with use of the equipment;
receiving first data including acceleration and angular velocity of the external device measured by the sensor attached to the equipment from the sensor through the communication interface;
calculating second data relating to the swing based on the first data; and
storing in the memory image data generated by the camera in association with the first data including the acceleration and the angular velocity of the external device measured by the sensor or the second data.

11. The non-transitory computer readable medium according to claim 10, wherein the process further comprises displaying an image generated from the image data, the first data, or the second data on a display.

12. The non-transitory computer readable medium according to claim 10, wherein the process further comprises storing a plurality of the first data or a plurality of the second data in the memory in chronological order.

13. The non-transitory computer readable medium according to claim 10, wherein the process further comprises storing data relating to a swing with respect to each of a plurality of types of equipment in the memory.

14. The non-transitory computer readable medium according to claim 10, wherein the process further comprises:
reading data of a professional golfer; and
performing comparison based on (i) the first data or the second data and (ii) the data of the professional golfer.

15. The non-transitory computer readable medium according to claim 14, wherein the process further comprises displaying (i) information based on the first data or information based on the second data and (ii) information based on the data of the professional golfer on a display in a comparable manner.

16. The non-transitory computer readable medium according to claim 10, wherein the process further comprises:
reading data of a professional golfer;
reading data obtained on a specific date from the first data or the second data stored in the memory; and
comparing the data of the professional golfer to the data obtained on the specific date.

17. The non-transitory computer readable medium according to claim 10, wherein the process further comprises storing the image data generated by the camera in association with the first data or the second data in the memory when the external device outputs a predetermined output.

18. The non-transitory computer readable medium according to claim 10, wherein the process further comprises starting the storing of the image data generated by the camera in the memory when the external device outputs a predetermined output.

19. The non-transitory computer readable medium according to claim 10, wherein the first data is at least one of data of acceleration and data of angular velocity.

20. The non-transitory computer readable medium according to claim 10, wherein the second data is data about a ratio of a practice of the swing performed with use of the equipment, a number of swings performed with use of the equipment, a speed of the swing performed with use of the equipment, a form of the swing performed with use of the equipment, a level of proficiency in the swing performed with use of the equipment, and a duration for which a swing is performed with use of the equipment.

21. The non-transitory computer readable medium according to claim 10, wherein the storing includes storing in the memory the image data generated by the camera in association with the first data including the acceleration and the angular velocity of the equipment measured by the sensor or the second data depending on the first data.

* * * * *